US012611485B2

(12) United States Patent (10) Patent No.: US 12,611,485 B2
Lee et al. (45) Date of Patent: Apr. 28, 2026

(54) COMPOSITE DEMINERALIZED BONE MATRIX COMPOSITION CONTAINING BONE MINERAL COMPONENT AND METHOD FOR PRODUCING SAME

(71) Applicant: L&C BIO CO., LTD., Seoul (KR)

(72) Inventors: Eun Seong Lee, Gwangmyeong-si (KR); Kee Won Lee, Seoul (KR); Hyung Gu Kim, Seoul (KR); Whan Chul Lee, Seoul (KR)

(73) Assignee: L&C BIO CO., LTD., Seoul (KR)

( * ) Notice: Subject to any disclaimer, the term of this patent is extended or adjusted under 35 U.S.C. 154(b) by 973 days.

(21) Appl. No.: 17/772,849

(22) PCT Filed: May 22, 2020

(86) PCT No.: PCT/KR2020/006685
§ 371 (c)(1),
(2) Date: Apr. 28, 2022

(87) PCT Pub. No.: WO2021/085775
PCT Pub. Date: May 6, 2021

(65) Prior Publication Data
US 2022/0378980 A1 Dec. 1, 2022

(30) Foreign Application Priority Data

Oct. 30, 2019 (KR) ........................ 10-2019-0136477
May 21, 2020 (KR) ........................ 10-2020-0060862

(51) Int. Cl.
*A61F 2/00* (2006.01)
*A61F 2/02* (2006.01)
(Continued)

(52) U.S. Cl.
CPC ............ *A61L 27/3608* (2013.01); *A61F 2/28* (2013.01); *A61L 27/26* (2013.01); *A61L 27/365* (2013.01);
(Continued)

(58) Field of Classification Search
None
See application file for complete search history.

(56) References Cited

U.S. PATENT DOCUMENTS 5,266,683 A * 11/1993 Oppermann ........... C07K 14/51
530/395
5,354,557 A * 10/1994 Oppermann .......... A61L 27/227
424/424
(Continued)

FOREIGN PATENT DOCUMENTS

CN 101631852 A * 1/2010 .............. A61P 35/00
CN 103957952 A 7/2014
(Continued)

OTHER PUBLICATIONS

FOR (Year: 2002).*
(Continued)

*Primary Examiner* — Ann Hu
(74) *Attorney, Agent, or Firm* — Panitch Schwarze Belisario & Nadel LLP

(57) ABSTRACT

A method for producing a composite demineralized bone matrix composition using a one-step process is described. The composite demineralized bone matrix composition is produced from the biologically-derived bone. In addition, the composite demineralized bone matrix composition contains bone minerals according to the original composition proportion in the bone and may provide a bone mineral content condition that is closest to that in an environment in which in vivo bone formation occurs. In addition, the
(Continued)

composition contains a bone morphogenetic protein (BMP-2), and thus enables a stable and excellent bone formation effect to be derived.

7 Claims, 7 Drawing Sheets

(51) Int. Cl.

| | |
|---|---|
| *A61F 2/28* | (2006.01) |
| *A61L 27/26* | (2006.01) |
| *A61L 27/36* | (2006.01) |
| *A61L 27/40* | (2006.01) |
| *A61L 27/54* | (2006.01) |

(52) U.S. Cl.
CPC ....... *A61L 27/3687* (2013.01); *A61L 27/3691* (2013.01); *A61L 27/40* (2013.01); *A61L 27/54* (2013.01); *A61F 2002/2817* (2013.01); *A61F 2002/2835* (2013.01); *A61L 2300/412* (2013.01); *A61L 2430/02* (2013.01); *A61L 2430/40* (2013.01)

(56) References Cited

U.S. PATENT DOCUMENTS

| | | | | |
|---|---|---|---|---|
| 7,132,110 | B2 | 11/2006 | Kay et al. | |
| 7,771,741 | B2 * | 8/2010 | Drapeau | A61L 27/446 |
| | | | | 424/488 |
| 8,147,860 | B2 | 4/2012 | Rosenberg et al. | |
| 8,992,965 | B2 * | 3/2015 | Behnam | A61K 35/32 |
| | | | | 424/549 |
| 10,251,976 | B2 * | 4/2019 | Erbe | A61L 27/46 |
| 2002/0143170 | A1 * | 10/2002 | Ni | C07K 14/51 |
| | | | | 435/7.1 |
| 2003/0224501 | A1 * | 12/2003 | Young | C07K 14/51 |
| | | | | 435/325 |
| 2004/0018595 | A1 * | 1/2004 | Rudolph | A61P 19/08 |
| | | | | 435/320.1 |
| 2007/0066525 | A1 * | 3/2007 | Lee | A61K 38/1875 |
| | | | | 514/8.8 |
| 2012/0213837 | A1 * | 8/2012 | Botchwey, III | A61P 17/02 |
| | | | | 514/114 |
| 2012/0213859 | A1 * | 8/2012 | Shelby | A61L 27/54 |
| | | | | 424/549 |
| 2013/0297038 | A1 * | 11/2013 | Mckay | A61L 27/3608 |
| | | | | 623/23.57 |
| 2015/0306278 | A1 * | 10/2015 | McKay | A61L 27/56 |
| | | | | 264/28 |
| 2017/0203006 | A1 * | 7/2017 | Carter | A61L 27/54 |
| 2018/0208635 | A1 * | 7/2018 | Zouani | A61P 11/06 |

FOREIGN PATENT DOCUMENTS

| | | | | | |
|---|---|---|---|---|---|
| KR | 20040048403 | A * | 6/2004 | ........ | A61L 27/3691 |
| KR | 10-2008-0113013 | A | 12/2008 | | |
| KR | 10-2013-0019997 | | 2/2013 | | |
| KR | 10-2013-0115781 | | 10/2013 | | |
| KR | 10-2014-0037908 | | 3/2014 | | |
| KR | 10-2015-0029988 | | 3/2015 | | |
| KR | 10-2017-0108194 | | 9/2017 | | |
| KR | 10-1885896 | B1 | 8/2018 | | |
| WO | WO-9721447 | A1 * | 6/1997 | ............. | A61P 43/00 |
| WO | WO-0061774 | A2 * | 10/2000 | ............... | A61P 9/10 |
| WO | WO-2005084701 | A1 * | 9/2005 | ............. | A61P 19/00 |

OTHER PUBLICATIONS

Office Action issued Feb. 22, 2022 in KR Application No. 10-2020-0060862.

Int'l Search Report issued Sep. 4, 2020 in Int'l Application No. PCT/KR2020/006685.

Alper et al, "Osteogenesis in bone defects in rats: the effects of hydroxyapatite and demineralized bone matrix," The American Journal of the Medical Sciences, vol. 298, No. 6, pp. 371-376 (1989).

Mcdonald et al, "Bone Morphogenetic Protein Concentration in Human Demineralized Bone Matrix," Transactions of the 51st Annual Meeting of the Orthopaedic Research Society: Washington, D.C., 1659 Materials and Methods: Results, Feb. 20-23, 2005.

Takuwa et al, "Bone morphogenetic protein-2 stimulates alkaline phosphatase activity and collagen synthesis in cultured osteoblastic cells, MC3T3-E1," Biochemical and Biophysical Research Communications, vol. 174, No. 1, pp. 96-101 (1991).

Urist, "Bone: Formation by Autoinduction," Science, vol. 150, No. 3698, pp. 893-899 (1965), Abstract only.

* cited by examiner

[FIG. 1]
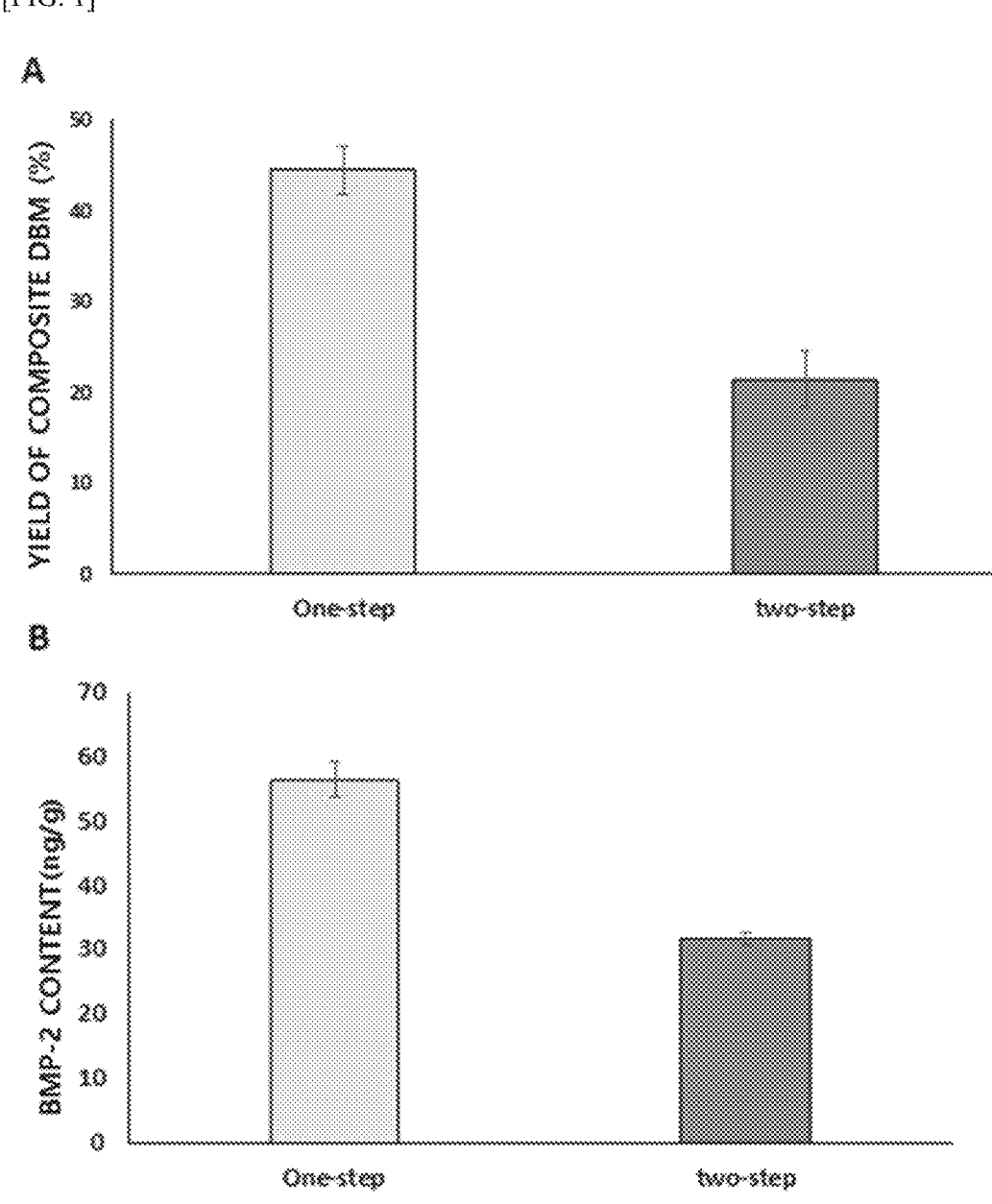

[FIG. 2]
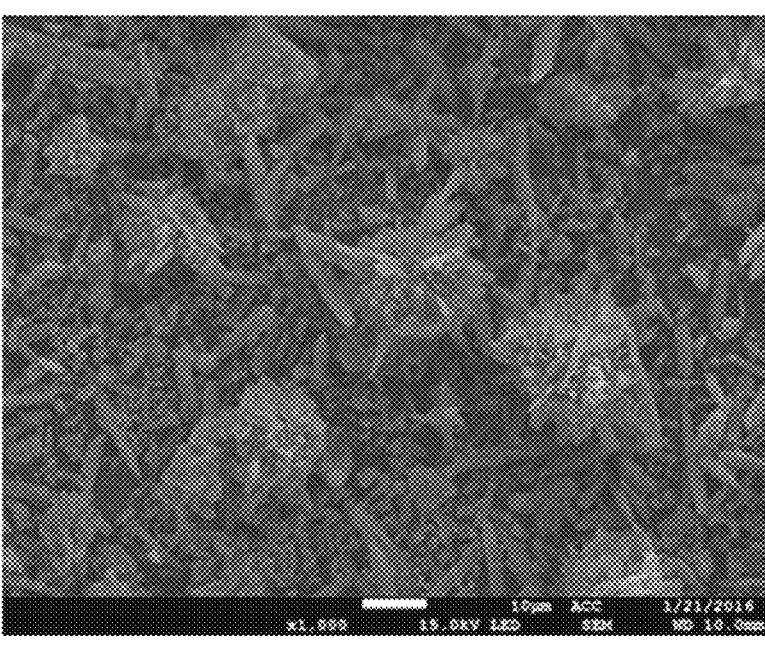
[FIG. 3]
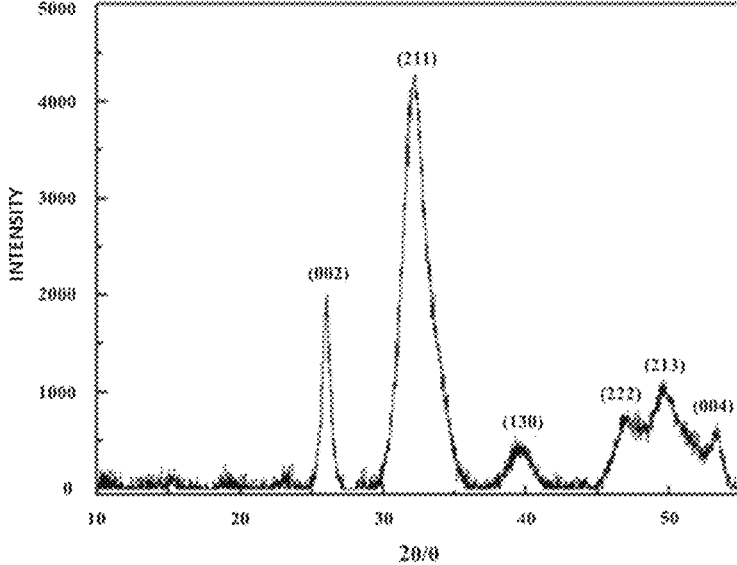

[FIG. 4]
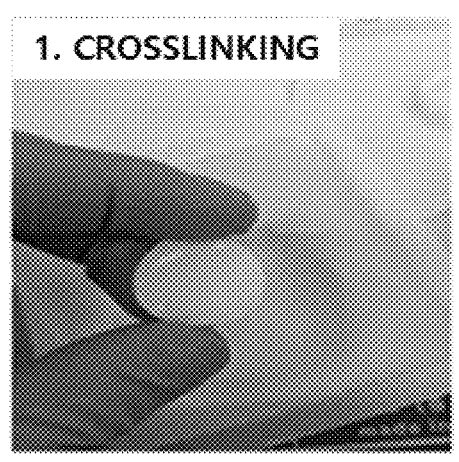
1. CROSSLINKING
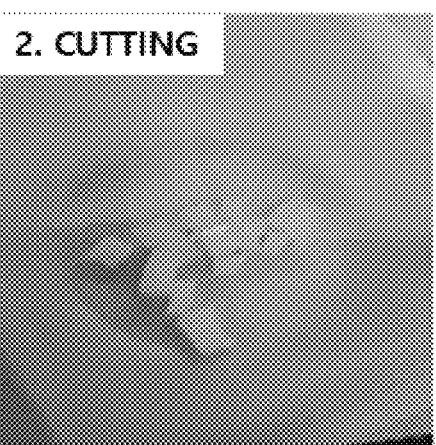
2. CUTTING
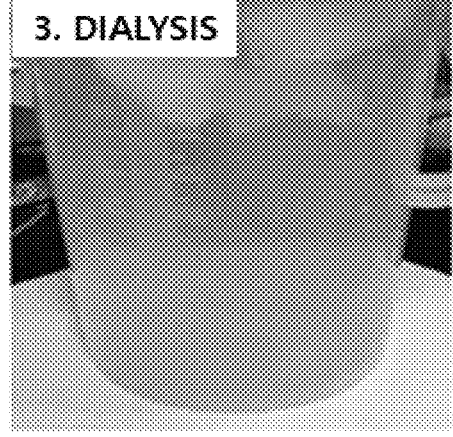
3. DIALYSIS
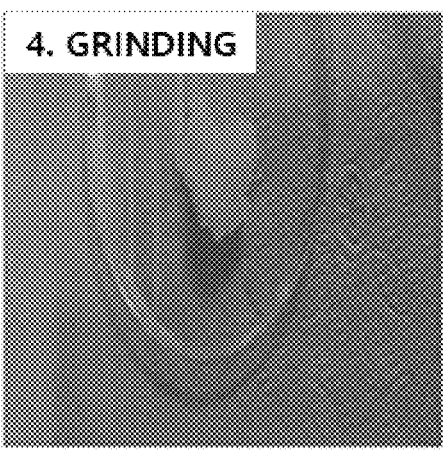
4. GRINDING

[FIG. 5]
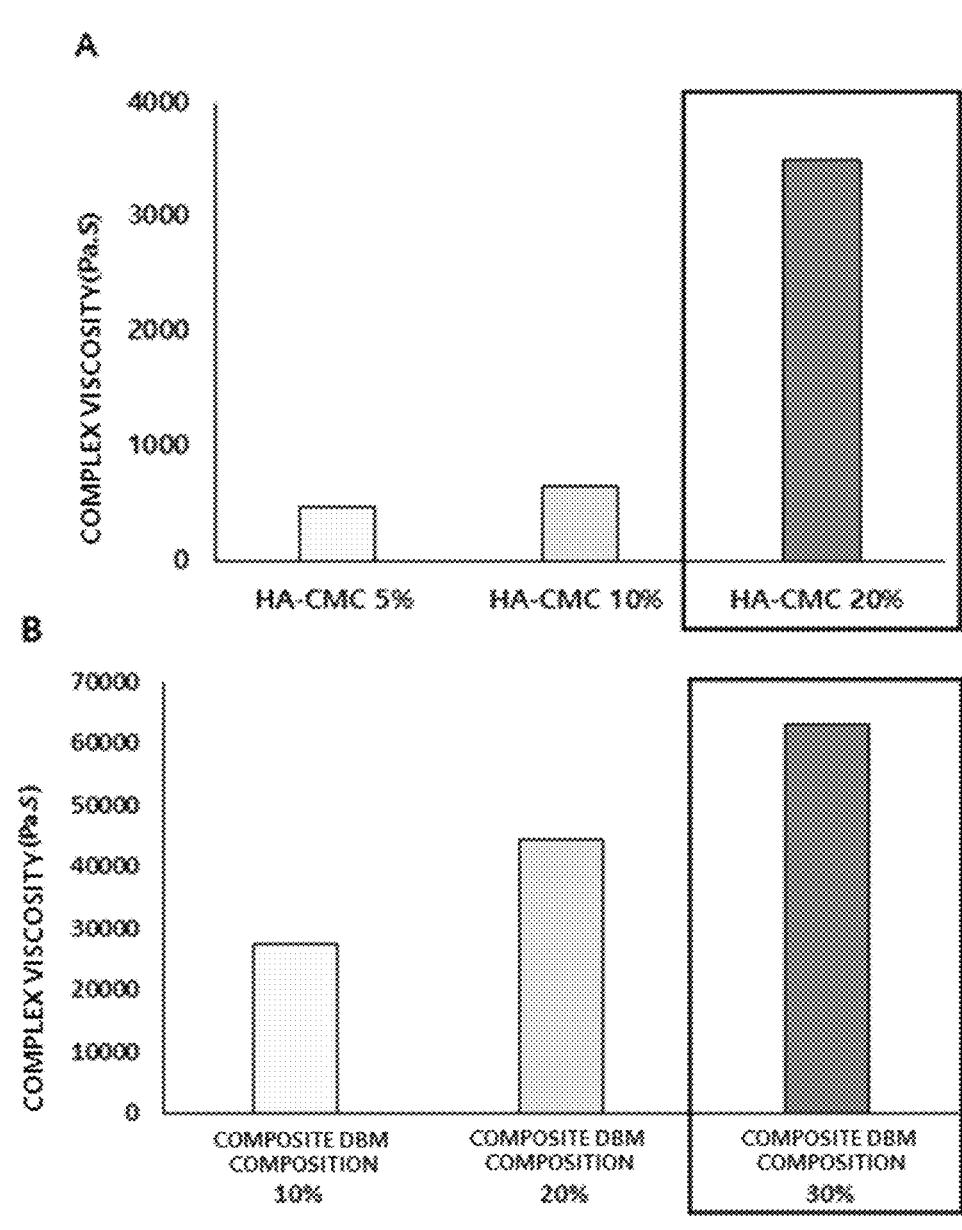

[FIG. 6]
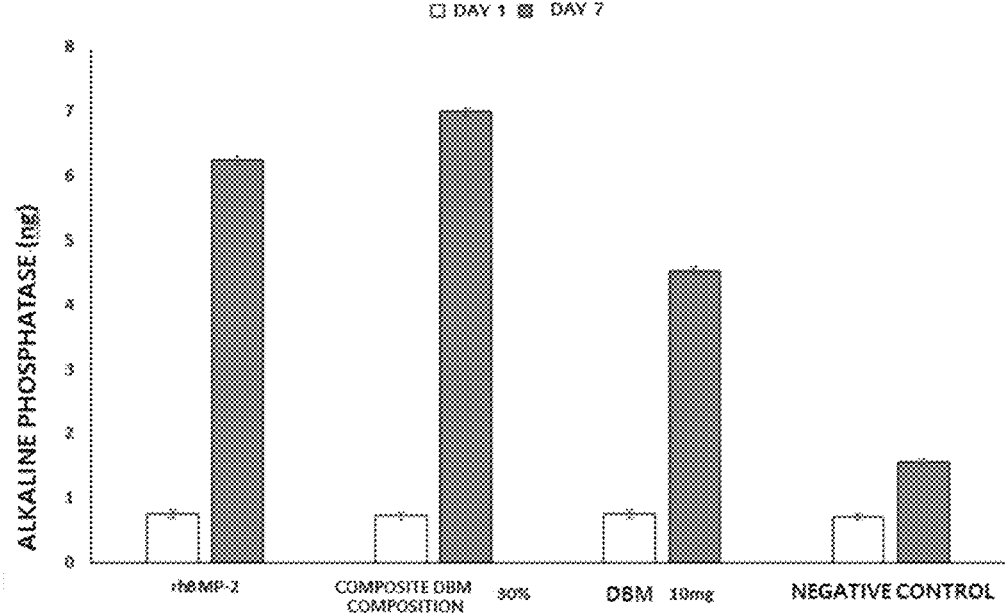

[FIG. 7]

| A | | |
|---|---|---|
| GRAFT MATERIAL | EXPERIMENTAL GROUP (ONE-STEP DMB GRAFT MATERIAL) | EXPERIMENTAL GROUP (TWO-STEP DMB GRAFT MATERIAL) |
| H&E Staining | | |
| GRAFT MATERIAL | EXPERIMENTAL GROUP (ONE-STEP DMB COMPOSITION PASTE) | EXPERIMENTAL GROUP (COMMERCIAL DMB GRAFT MATERIAL CONTAINING DMB ALONE) |
| H&E Staining | | |

[FIG. 8]
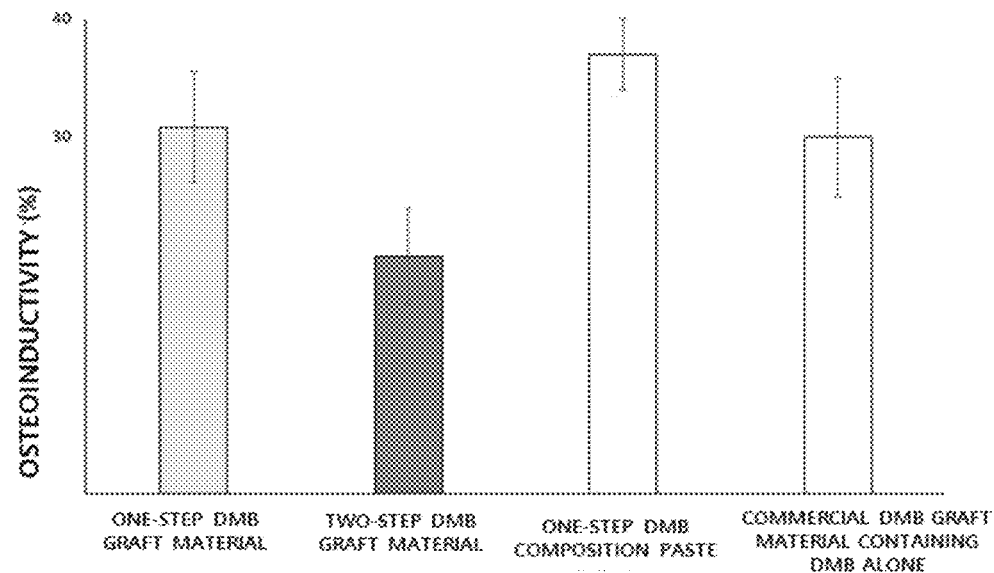

COMPOSITE DEMINERALIZED BONE MATRIX COMPOSITION CONTAINING BONE MINERAL COMPONENT AND METHOD FOR PRODUCING SAME

CROSS-REFERENCE TO RELATED APPLICATIONS

This application is a Section 371 of International Application No. PCT/KR2020/006685, filed May 22, 2020, which was published in the Korean language on May 6, 2021 under International Publication No. WO 2021/085775 A1, which claims priority under 35 U.S.C. § 119(b) to Korean Application No. 10-2019-0136477, filed Oct. 30, 2019, and Korean Application No. 10-2020-0060862, filed May 21, 2020, the disclosures of which are incorporated herein by reference in their entireties.

TECHNICAL FIELD

The present invention relates to a composite demineralized bone matrix composition including bone mineral and a demineralized bone matrix and a method of preparing the same. In addition, the present invention relates to a composite composition for bone grafting, which includes bone minerals, a demineralized bone matrix, and a polymer excipient.

Specifically, the present invention relates to a composite demineralized bone matrix (DBM) composition in which bone minerals obtained from a bio-derived bone and a DBM are mixed in a composition ratio similar to the original bone, a one-step process for preparing the same, and a biopolymer excipient maintaining the formulation of the composite DBM composition.

TECHNICAL FIELD

In line with the increase in the aging population, the increase in surgical accident rate due to the diversification of the industrial society and the development of medical procedures, the demand, and necessity for bone graft materials for bone regeneration are increasing, and the demand for technology for safer and more effective bone graft materials with excellent osteogenesis is also increasing.

Conventionally, bone graft materials may be classified into autografts, xenografts, synthetic bone grafts and allografts. Autologous bone grafting has the advantage of being relatively free from immune responses compared to non-autologous bone grafting or synthetic bone grafting. In autologous bone grafting, not only a patient's bone matrix but also autologous cells are implanted, so autografts are relatively advantageous in terms of osteogenesis, compared to other graft materials, and have excellent osteoinductivity and osteoconductivity. However, it is difficult to obtain an autograft in a sufficient amount necessary for the procedure, and also is not easy to obtain an autograft with a desired shape. In addition, autologous bone grafting may be accompanied by an incision and bleeding caused by additional surgery at a bone donor site, the occurrence of hematomas and fractures, and may require a transfusion, and may cause problems such as nerve damage, sensory loss, and chronic pain and instability of the bone donor site. Xenografts have no osteoinductivity but appeared to compensate for the shortcomings of autograft collection. However, the xenografts have a disadvantage of having a lower bone-forming rate and lower new osteogenesis than autografts and allografts. Synthetic bone grafts that have no osteoinductivity are obtained by extracting calcium carbonate using natural coral or chemically made using calcium carbonate and calcium phosphate. Such a synthetic bone graft is synthesized in a calcium-to-phosphorus ratio (Ca/P ratio) of 1.67, which is similar to the Ca/P ratio of human bone tissue. Synthetic bone grafts have an advantage of low toxicity in the body, but shortcomings such as a low internal resorption rate and low strength remain. Finally, since allografts, unlike autografts, do not have bone-forming cells, they have no direct osteogenesis. Allografts do not have osteoinductivity in which osteoprogenitor cells are stimulated to differentiate into osteoblasts and only have osteoconductivity which provides a space in which bone formation occurs in tissue adjacent to a region in which grafting will occur. However, since it is possible to obtain allografts at a sufficient amount for the procedure, there is an advantage in that it is not necessary to obtain autografts with difficulty. Such allografts have only osteoconductivity without osteoinductivity because a bone morphogenetic protein (BMP), which is trapped by calcium phosphate that is a mineral among bone components, does not properly function. For this reason, an allograft, which is DBM, has been developed for BMPs to be suitably involved in osteoinduction. Generally, DBM is made through demineralization which removes a mineral component from the bone. Demineralization generally uses acidic solvents, and there are various demineralization methods according to the type of acidic solvent. Due to such a demineralization process, organic components (the extracellular matrix and trace amounts of BMPs) from which inorganic substances are eliminated are removed from the original bone, so there is a disadvantage in the process in that BMPs are formed in a state of being deficient in bone mineral helping bone formation.

Bone mineral, accounting for 65 to 70% of human bone, is a component helping bone regeneration and consists of calcium (Ca), phosphorus (P), iron (Fe), potassium (K), magnesium (Mg), sodium (Na) and zinc (Zn). The bone mineral is mostly present in the form of hydroxyapatite (HAp) consisting of calcium and phosphorus and contains trace amounts of minerals such as iron, potassium, magnesium, sodium, and zinc. Synthetic HAp products have a single formulation consisting of only calcium and phosphorus, which inevitably is a different mineral component ratio from that of real human-derived bone minerals.

When bone mineral that can be obtained from an allograft is implanted together with DBM, it is possible to create an environment very close to the bone-forming condition that the human body has in a natural state, and it is known that a HAp-derived bone graft material as a bone mineral has osteoconductivity, and DBM prepared as an allograft has excellent osteoinductivity. Therefore, it is estimated that, when the bone mineral is implanted together with DBM, compared to the use of DBM alone, this combination has osteoinductivity as well as osteoconductivity, and thus can provide relatively excellent osteogenesis. The composite DBM composition for bone grafting according to the present invention, which is formulated to include not only the bone mineral component but also a DBM component, has both osteoconductivity and osteoinductivity, which are required for bone formation. Moreover, the bone mineral has excellent osteogenesis since it contains essential minerals in bone formation Generally, in DBM preparation, only DBM is obtained, and a demineralization solution generated after demineralization is discarded. Alternatively, a two-step process for obtaining two types of products in the forms of a DBM powder and a bone mineral powder by performing separate preparation processes including a step of obtaining DBM and a step of extracting a bone mineral component from a demineralization solution is used. In the two-step process, immediately after demineralization, DBM and the demineralization solution are completely separated, and DBM is washed several times, followed by obtaining powder-type DBM through lyophilization. Meanwhile, the demineralization solution separately isolated and recovered is sequentially subjected to filtration, neutralization, centrifugation, washing with distilled water, and lyophilization, resulting in a fine bone mineral powder. In this overlapping preparation process, DBM and the bone mineral are lost before the final yield. In addition, even when mixing is performed based on any one of the obtained DBM and bone minerals, the component ratio may not be adjusted to that of the original bone. That is, if there is no artificially discarded product, DBM and the bone mineral are inevitably in an arbitrary ratio.

In addition, as an essential procedure for obtaining bone minerals from the demineralization solution in the two-step process, a neutralization method through pH titration is used. NaOH is generally used, and the optimal pH range is used approximately 6.0 to 7.5. Immediately after neutralization, the bone mineral components are formed as precipitates from the demineralization solution, some protein-type bioactive materials released from DBM are also prepared as precipitates together with the bone mineral. In one example, it is well known that BMP-2 is formed as a precipitate at pH 6.2 or more, and dissolved at pH 6.2 or less. The conventional art for obtaining bone minerals does not describe a method of obtaining such a bioactive material released from DBM together with bone minerals. Furthermore, according to the conventional art, since a bone mineral powder purified by purification and washing with distilled water is obtained immediately after bone mineral sedimentation, the bioactive material may be redissolved in distilled water in the process of washing with distilled water several times and lost.

Therefore, the present invention will suggest a one-step process that can obtain DBM aminerals mineral in one preparation method, rather than separately obtaining them, and a method of preparing a composite DBM composition maintaining a bone mineral content ratio that is closest to that of the original human bone.

In addition, the present invention is intended to suggest a method of exposing some physiologically-active materials such as BMP-2 to the outside of DBM using a weakly-acidic solvent in a one-step process and a preparation method of obtaining the exposed physiologically-active material when DBM and bone mineral are obtained.

In addition, the present invention will suggest a method of producing a biocompatible hydrogel-type excipient that can maximize bone formation when the composition of the present invention is implanted into the body while being well agglomerated based on an affected area without being scattered in a powder state. Specifically, the present invention will suggest a method of preparing a paste-type composition for bone grafting having excellent moldability by applying an excipient containing hyaluronic acid, which is a biopolymer, to a composite DBM composition obtained through a one-step process.

Non-Patent Documents

1. URIST, Marshall R. Bone: Formation by autoinduction. Science, 1965, 150.3698:893-899.

2. ALPER, Glenn, et al. Osteogenesis in bone defects in rats: the effects of hydroxyapatite and demineralized bone matrix. The American Journal of the Medical Sciences, 1989, 298.6:371-376.
3. TAKUWA, Yoh, et al. Bone morphogenetic protein-2 stimulates alkaline phosphatase activity and collagen synthesis in cultured osteoblastic cells, MC3T3-E1. Biochemical and Biophysical Research Communications, 1991, 174.1:96-101.

DISCLOSURE

Technical Problem

The present invention is directed to providing a composite demineralized bone matrix (DBM) composition containing bone minerals obtained from the bio-derived bone in an amount closest to the composition ratio of the original human bone and a method of preparing the same.

In addition, the present invention is directed to providing a composite DBM composition containing a bioactive material exhibiting an effect on bone growth and bone formation and a method of preparing the same.

In addition, the present invention is directed to providing a method of preparing a composite DBM composition containing bone minerals in a composition ratio of the original bone in a one-step process.

In addition, the present invention is directed to providing a paste-type composition for bone grafting using a biocompatible polymer excipient to have excellent cohesiveness and increase convenience in medical use.

Technical Solution

The present invention provides a method of preparing a composite DBM composition using a one-step process, which includes:

a demineralization step of demineralizing bone tissue with an acidic solution;

a bone mineral precipitation step of precipitating bone mineral by neutralizing the demineralized solution with an alkaline solution;

a BMP-2 extraction step of extracting BMP-2 by centrifuging the solution in which the precipitation is completed and adding an acidic solution to a pellet; and a composite DBM composition preparation step of precipitating the DBM, the bone mineral, and the BMP-2 by neutralizing the BMP-2-extracted solution with an alkaline solution.

In addition, the present invention provides a composite DBM composition including DBM, bone mineral, and BMP-2, which is prepared by the above-described method of preparing the composite DBM composition using a one-step process.

In addition, the present invention provides a composition for bone grafting, which includes: the above-described composite DBM composition; and a biocompatible polymer or a crosslinking product of the biocompatible polymer.

Advantageous Effects

In the present invention, a demineralized bone matrix (DBM) composition and bone mineral can be obtained together in a one-step process, rather than separately obtaining them in separate processes, and thus a composite DBM composition having a bone mineral content ratio closest to the composition ratio of the bone mineral contained in the original human bone can be prepared.

Accordingly, since the composite DBM composition prepared by the one-step process according to the present invention contains bone minerals obtained from the bio-derived bone in a composition ratio of the original bone, a mineral content condition closest to an environment in which bone formation occurs in the body can be provided, so the composite DBM composition is more stable. In addition, the composite DBM composition sufficiently contains proteins effective in bone growth and bone formation and has excellent osteoconductivity and osteoinductivity. Therefore, an excellent bone-forming effect can be achieved.

In addition, in the present invention, since the composite DBM composition is mixed with a hydrogel-type excipient, when the DBM is implanted into the body, it can be implanted while being well agglomerated based on an affected area without being scattered in a powder state to maximize bone formation and can have biocompatibility.

DESCRIPTION OF DRAWINGS

FIG. 1 shows the results of the yields of composite demineralized bone matrix (DBM) compositions prepared in a one-step process and a two-step process and BMP-2 contents in the composite DBM compositions.

FIG. 2 shows an SEM image of bone mineral in a composite DBM composition.

FIG. 3 shows the result of X-ray diffraction analysis on the unique crystal structure of the bone mineral.

FIG. 4 shows the procedure of preparing an HA-CMC excipient (carrier) according to the present invention.

FIG. 5 shows the results of measuring complex viscosities of an HA-CMC excipient and a composite DBM composition prepared according to embodiments of the present invention.

FIG. 6 shows the result of an ALP assay of a composite DBM composition prepared according to an embodiment of the present invention.

FIGS. 7 and 8 show the results of evaluating osteoinductivity in vivo.

MODES OF THE INVENTION

The present invention relates to a method of preparing a composite demineralized bone matrix (DBM) composition using a one-step process, which includes:

a demineralization step of demineralizing bone tissue with an acidic solution;

a bone mineral precipitation step of precipitating bone mineral by neutralizing the demineralized solution with an alkaline solution;

a BMP-2 extraction step of extracting BMP-2 by centrifuging the solution in which the precipitation is completed and adding an acidic solution to a pellet; and a composite DBM composition preparation step of precipitating the DBM, the bone mineral, and the BMP-2 by neutralizing the BMP-2-extracted solution with an alkaline solution.

In one embodiment of the present invention, a composite DBM composition was prepared in a one-step process and it was confirmed that the prepared composite DBM composition has a bone mineral content ratio closest to the composition ratio of bone mineral that is contained in the original human bone.

In addition, a composition for bone grafting, which includes the composite DBM composition and crosslinking product of a biocompatible polymer (HA-CMC excipient), was prepared and it was confirmed that the composition for bone grafting has excellent viscoelasticity. In addition, an in vivo experiment was conducted on the composition for bone grafting to confirm that the composition according to the present invention has excellent osteoinductivity.

Hereinafter, the method of preparing a composite DBM composition according to the present invention will be described in further detail.

The term "demineralized bone matrix (DBM)" used herein refers to a rubber-type material that is semi-transparent and flexible, and has a bone morphogenetic protein (BMP) promoting bone growth therein. The DBM may be a raw material for a good graft material that can promote bone formation.

The term "demineralized" used herein refers that a mineral being extracted from a bio tissue including minerals such as calcium using a chelating agent. Generally, in a "demineralization solution" obtained by demineralizing bone tissue, a large number of mineral components such as calcium phosphate constituting human bone are included.

The term "one-step process" used herein refers to a process for obtaining both DBM and bone mineral in one reactor, rather than separately obtaining them with different processes in the preparation of a composite DBM composition.

In addition, in the present invention, since both DBM and the bone mineral may be obtained in the one-step process, the composition obtained from both the DBM and the bone mineral may be expressed as a composite DBM (composite mineral-DBM) composition.

In general, a composition for bone grafting includes DBM and bone minerals, and is prepared using a two-step process including a step of obtaining DBM and a step of extracting a bone mineral component from a demineralization solution, which is performed separately. The preparation method using the two-step process has a loss of DBM and the bone mineral until the final yield thereof, and a problem that the component ratio of the original bone cannot be matched even when mixing is performed based on any one of the obtained DBM and bone mineral. In addition, the conventional two-step process does not include a bioactive material such as BMP-2.

Accordingly, in the present invention, when a composite DBM composition is prepared using a one-step process, both DBM and bone mineral may be obtained in one preparation process, thereby simplifying the process, and a composition that can maintain the bone mineral content ratio closest to the composition ratio of minerals contained in the original human bone may be prepared. In addition, a composition containing a bioactive material may be prepared.

The method of preparing a composite DBM composition using a one-step process according to the present invention includes (S1) a demineralization step; (S2) a bone mineral precipitation step; (S3) a BMP-2 extraction step; and (S4) a composite DBM composition preparation step.

In the present invention, before step (S1), a washing step of washing bone tissue may be additionally performed. As a washing solvent, isopropyl alcohol, sterile water or a mixture thereof may be used. Through this step, impurities in the bone tissue may be removed.

In the present invention, (S1) the demineralization step is a step of demineralizing bone tissue with an acidic solution.

In the present invention, the bone tissue may be autologous or heterologous bone tissue. The autologous bone tissue may mean human-derived bone tissue, and the heterologous bone tissue may mean bone tissue derived from an animal other than a human, which is a mammal-derived bone tissue such as a porcine, bovine or equine bone tissue.

In one embodiment, the bone tissue may be cortical bone.

In one embodiment, the bone tissue may be provided as a powder. Here, the bone tissue may have an average particle diameter of 20 to 800 μm.

In one embodiment, the type of acidic solution is not particularly limited as long as it can demineralize bone tissue, and the acidic solution may be, for example, an acidic solution of one or more selected from hydrochloric acid, ethylenediaminetetraacetic acid (EDTA), formic acid, citric acid, acetic acid, nitric acid and nitrous acid.

The concentration and content of the acidic solution used may be suitably selected according to a selected acid.

In one embodiment, demineralization may be performed with 10 to 50 ml of a 0.5 to 1.5N hydrochloric solution per 1 g of bone tissue.

In one embodiment, demineralization may be performed at pH 1 to 3.

In addition, demineralization may be performed for 1 to 10 hours in one embodiment.

In the present invention, (S2) the bone mineral precipitation step is a step of precipitating bone mineral by neutralizing the resulting solution that has been demineralized in (S1) with an alkaline solution.

The demineralization solution that has undergone (S1) consists of a supernatant and a precipitate, wherein the precipitate contains DBM. In the present invention, according to the preparation method using a one-step process, a composite DBM composition having a bone mineral content ratio closest to the composition ratio of bone mineral contained in the original human bone may be prepared without separating DBM as the precipitate.

In one embodiment, the type of alkaline solution is not particularly limited, and the alkaline solution may be one or more selected from the group consisting of sodium hydroxide (NaOH) and phosphate-buffered saline. Alternatively, as the alkaline solution, commercially available physiological saline, a 0.9% sodium chloride solution or sterile water was used for washing several times, or added for neutralization.

In one embodiment, the bone mineral precipitation step may be to neutralize the demineralized solution with a 0.5 to 4.0M sodium hydroxide (NaOH) solution. In one embodiment, the neutralization may be performed until the pH of the demineralization solution reaches 5.5 to 7.0.

In addition, in one embodiment, the bone mineral precipitation step may be performed for 0.5 to 4 hours.

In the present invention, (S3) the BMP-2 extraction step is a step of extracting BMP-2 by centrifuging the solution in which the precipitation is completed obtained in (S2) and adding an acidic solution to a pellet.

The DBM prepared in (S1) is sedimented by centrifugation, and the bone mineral precipitated in (S2) is also sedimented, thereby forming a pellet. Accordingly, in the present invention, the supernatant may be removed through centrifugation, and the resulting pellet containing an active component may be obtained.

In one embodiment, the centrifugation may be performed at 1,000 to 8,000 rpm for 10 to 30 minutes, and the resulting pellet obtained thereby may be washed with sterile water.

In one embodiment, the centrifugation and washing may be repeated once to three times.

Meanwhile, a bone morphogenetic protein (BMP) is involved in osteoinduction. The BMP, particularly, BMP-2, is generated as a precipitate at pH 6.2 or more, and is present while being dissolved at pH 6.2 or less. Conventional techniques for obtaining bone minerals can obtain a bone mineral powder purified by purification and washing with distilled water immediately after bone mineral sedimentation, so a bioactive material may be lost by being redissolved in distilled water in the process of washing with distilled water several times.

In the present invention, as a separate process for extracting BMP-2 is provided, a composite DBM composition that has not only DBM and bone mineral but also a sufficient amount of a bioactive component may be prepared.

In one embodiment, as an acidic solution for extracting BMP-2, the above-described acidic solution, that is, a solution of one or more acids selected from the group consisting of hydrochloric acid, guanidine hydrochloride, ethylenediaminetetraacetic acid (EDTA), formic acid, citric acid, acetic acid, nitric acid and nitrous acid may be used. In the present invention, the acidic solution may be replaced with urea.

The concentration and content of the acidic solution used may be suitably adjusted according to the selected acid.

In one embodiment, the BMP-2 may be extracted by adding acetic acid to the precipitate.

In one embodiment, the BMP-2 extraction may be performed at pH 4 to 6.5. In the above-described pH range, BMP-2 is easily extracted, and can be quantified.

In addition, in one embodiment, the BMP-2 extraction may be performed for 1 to 72 hours.

In the present invention, (S4) the composite DBM composition preparation step is a step of precipitating the DBM, the bone mineral and the BMP-2 by neutralizing the BMP-2-extracted solution obtained in (S3) with an alkaline solution.

In one embodiment, the type of alkaline solution is not particularly limited, and the alkaline solution may be one or more selected from the group consisting of sodium hydroxide (NaOH) and phosphate-buffered saline.

In one embodiment, the neutralization may be performed until the pH of the solution reaches 6.2 to 6.8.

In one embodiment, the composite DBM composition preparation step may be to precipitate DBM, the bone mineral and BMP-2 by neutralizing the demineralized solution with a 0.5 to 4.0M sodium hydroxide (NaOH) solution.

In addition, the above-described step may be performed for 0.5 to 72 hours in one embodiment.

In the present invention, after (S4) the composite DBM composition preparation step, a washing step for washing the resulting pellet may be further included.

In one embodiment, the resulting pellet may be washed with sterile water once to three times, and may be centrifuged.

In addition, in the present invention, after (S4) the composite DBM composition preparation step and/or the washing step, a drying step may be further performed.

In one embodiment, the drying may be performed by lyophilization, and the lyophilization may be performed at −50 to −80° C. for 24 to 96 hours.

The water content in the dried product of the present invention may be 10% or less, and preferably 1 to 8%.

The composite DBM composition prepared by the preparation method according to the present invention may have DBM and bone mineral mixed in a range approximate to the composition ratio of human bone, and may be prepared by obtaining DBM and the bone mineral only in a one-step process, rather than separate processes.

In addition, the present invention relates to a composite DBM composition prepared by the above-described preparation method.

The composite DBM composition prepared using a one-step process according to the present invention may include DBM, bone mineral and BMP-2, and DBM and the bone mineral may be mixed in a range approximate to the human bone composition ratio.

In one embodiment, the DBM content may be 5 to 30 wt % or 10 to 20 wt % with respect to the total weight of the composition. In addition, the bone mineral content may be 10 to 50 wt % or 20 to 40 wt % with respect to the total weight of the composition.

In one embodiment, the bone mineral may include 34 to 47 wt % of calcium, 15 to 21 wt % of phosphorus, 0.358 to 0.373 wt % of magnesium, 0.079 to 0.143 wt % of sodium, 0.014 to 0.015 wt % of zinc, 0.015 to 0.02 wt % of potassium and 0.00015 to 0.0025 wt % of iron.

In one embodiment, the composite DBM composition may include 1 ng/g to 100 ng/g of BMP-2. The difference between the minimum and maximum contents may be caused by variation according to a donor.

In addition, the present invention relates to a composition for bone grafting, which includes the composite DBM composition prepared by the above-described preparation method.

The composition for bone grafting according to the present invention may include a biocompatible polymer or a crosslinked product thereof in addition to the composite DBM composition. Since the composition for bone grafting includes a biocompatible polymer or a crosslinked product thereof and has a paste form, the composition for bone grafting may be expressed as a paste for bone grafting, or as a composite DBM paste.

In one embodiment, the composite DBM composition may be provided as a powder, and the average particle diameter of the powder may be adjusted to a suitable size for injection into the body.

In one embodiment, the content of the composite DBM composition may be 10 to 90 parts by weight, 10 to 30 parts by weight or 20 to 30 parts by weight with respect to the total weight (100 parts by weight) of the composition for bone grafting. In the above range, the composition may have excellent bone regeneration ability.

In the present invention, the biocompatible polymer or the crosslinked product thereof may improve a viscoelastic property of the composition for bone grafting, and improve body volume retention. In the present invention, the biocompatible polymer or the crosslinked product thereof may be expressed as an excipient (or a carrier).

In one embodiment, the crosslinked product of the biocompatible polymer refers to one or more biocompatible polymers which are chemically crosslinked.

In one embodiment, the molecular weight of the biocompatible polymer or the crosslinked product thereof may be 10 kDa to 2 MDa.

In one embodiment, the biocompatible polymer may be one or more selected from the group consisting of collagen, hyaluronic acid, chitosan, carboxymethylcellulose, alginate and gelatin.

In one embodiment, the crosslinked product of the biocompatible polymer may be a crosslinked product of one or more biocompatible polymers selected from the group consisting of collagen, hyaluronic acid, chitosan, carboxymethylcellulose, alginate and gelatin. Specifically, in the present invention, a crosslinked product of sodium hyaluronate (HA) and sodium carboxymethyl cellulose (CMC) may be used.

In one embodiment, the biocompatible polymer may be crosslinked by a crosslinking agent, which may be one or more selected from the group consisting of 1,4-butanediol diglycidyl ether (BDDE), ethylene glycol diglycidyl ether (EGDGE), 1,6-hexanediol diglycidyl ether, propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylpropane polyglycidyl ether, 1,2-(bis(2,3-epoxypropoxy)eth-ylene, pentaerythritol polyglycidyl ether, and sorbitol polyglycidyl ether.

In one embodiment, the content of the biocompatible polymer or a crosslinked product thereof may be 5 to 90 parts by weight, 5 to 30 parts by weight or 5 to 20 parts by weight with respect to the total weight (100 parts by weight) of the composition for bone grafting. In the above range, the physical properties of the biocompatible polymer may be improved.

In one embodiment, the complex viscosity of the paste for bone grafting may be 1,000 to 100,000 Pa·s. The complex viscosity refers to a value measured by a rotary rheometer analyzer (frequency: 0.1~100 Hz, temperature: 25° C., strain: 1%).

The complex viscosity is a frequency-dependent viscosity calculated by a vibration measurement method, and the value is a number that reflects G" (viscous modulus (loss modulus)), G' (elastic modulus (storage modulus)) and a frequency value to be measured.

In one embodiment, the composition for bone grafting of the present invention may be injected or inserted into the body. The composition for bone grafting may be used as a general medical material.

In addition, the present invention relates to a method of preparing the above-described composition for bone grafting.

The method of preparing the composition for bone grafting includes mixing a composite DBM composition; and a biocompatible polymer or a crosslinked product thereof.

As the composite DBM composition of the present invention, the composite DBM composition prepared by the above-described preparation method may be used.

Specifically, the composite DBM composition of the present invention may be prepared by a demineralization step of demineralizing bone tissue with an acidic solution;

a bone mineral precipitation step of precipitating bone mineral by neutralizing the demineralized solution with an alkaline solution;

a BMP-2 extraction step of extracting BMP-2 by centrifuging the solution in which the precipitation is completed and adding an acidic solution to a pellet; and a composite DBM composition preparation step of precipitating the DBM, the bone mineral and the BMP-2 by neutralizing the BMP-2-extracted solution with an alkaline solution.

In the present invention, as the biocompatible polymer or a crosslinked product thereof, a commercially available product may be used. In addition, the crosslinked product may be prepared and used in a laboratory using the biocompatible polymer.

The crosslinked product of the biocompatible polymer may be prepared by a crosslinking step of crosslinking a biocompatible polymer using a crosslinking agent;

a dialysis step of dialyzing the crosslinked product; and a grinding step of grinding the dialyzed crosslinked product.

In the present invention, the crosslinking step is a step of crosslinking the biocompatible polymer using a crosslinking agent. In this step, the biocompatible polymer and the crosslinking agent may be the above-described types.

In one embodiment, the biocompatible polymers may be bonded by amide bonds.

In one embodiment, the content of the crosslinking agent may be 0.5 to 10 parts by weight with respect to the biocompatible polymer.

In the present invention, before lyophilization, a step of washing the crosslinked reaction product may be further performed. Here, as a washing solution, phosphate-buffered saline (PBS) and/or sterile water may be used.

In the present invention, before dialysis, a step of cutting the crosslinked product may be further included.

In the present invention, the dialysis step may be performed using phosphate-buffered saline.

In addition, the grinding step may be performed using a grinder which is generally used in the art. In the present invention, before the grinding step, lyophilization may be further performed.

In the present invention, a composite DBM composition; and a biocompatible polymer or a crosslinked product thereof may be mixed by physical mixing.

In one embodiment, the content of the composite DBM composition in the physically mixed mixture may be 10 to 90 parts by weight, 10 to 30 parts by weight or 20 to 30 parts by weight.

In addition, the content of the biocompatible polymer or the crosslinked product thereof in the mixture may be 5 to 90 parts by weight, 5 to 30 parts by weight or 5 to 20 parts by weight.

In one embodiment, the mixture may be prepared by dissolving the crosslinked product of the biocompatible polymer in a solvent, and mixing the dissolved resultant with the composite DBM composition. Here, as the solvent, physiological saline may be used.

The present invention may further include a step of sterilizing the mixture.

Through the sterilization step, immunity in the composition for bone grafting may be eliminated, and bacteria may be effectively killed.

In one embodiment, the sterilization step may be performed by irradiation, and the irradiation range may be 10 to 30 kGy.

In addition, the present invention relates to the use of the above-described composition for bone grafting.

The composition for bone grafting according to the present invention may induce bone regeneration after transplantation into the body.

The present invention will be described in further detail regarding the following examples. However, the scope of the present invention is not limited to the following examples, and it will be understood by those of ordinary skill in the art that various changes, modifications or applications are possible in the scope without departing from the technical matters derived from the details described in the accompanying claims.

EXAMPLES

Example 1. Preparation of Composite DBM Composition Through an One-Step Process

A pretreatment process in which cortical bone was washed with isopropyl alcohol (2-propanol for analysis EMSURE® ACS, ISO, Reag. Ph Eur, Merck), and then washed with sterile water was performed.

Afterward, 1 g of the cortical bone was demineralized using 10 to 50 ml of 0.5 to 1.5N hydrochloric acid (35.0-37.0%, JUNSEI CHEMICAL CO., LTD.) at room temperature for 4 hours. A mixture of a supernatant and a precipitate, obtained through the demineralization, was treated with a 0.5 to 4.0M sodium hydroxide (NaOH, Sodium hydroxide, Merck) solution to induce the precipitation of the bone mineral from the mixture and sedimentation along with DBM. The mixed solution in which the sedimentation and the precipitation were completed was centrifuged at 1,000 to 8,000 rpm for 10 to 30 minutes to remove supernatant. After the centrifugation, the supernatant was removed, and the resulting pellet was washed with sterile water once to three times.

BMP-2 was extracted from the washed pellet using acetic acid. The mixed solution in which the extraction had been completed was titrated to adjust the pH thereof to 6.2 to 6.8 using a 0.5 to 4.0M sodium hydroxide solution, thereby precipitating DBM, the bone mineral and the extracted BMP-2. After the resulting precipitate was washed once to three times with sterile water and centrifuged, lyophilization was performed to have a water content of 10% or less, and preferably 1 to 8%.

The material obtained through lyophilization, that is, the composite DBM composition, is a mixture of DBM and the bone mineral in a range approximate to the composition ratio of human bone. In the present invention, a composite DBM composition was obtained with DBM and the bone mineral which was obtained in a one-step process, not by separate processes.

Comparative Example 1. Obtaining Power-Type Composite DBM Composition Through a Two-Step Process 10 g of cortical bone was demineralized using 200 ml of 0.5N hydrochloric acid for 2 hours while being stirred at room temperature. A demineralization solution was recovered, and the demineralized bone powder was recovered, followed by processing DBM according to a DBM processing process.

To remove the remaining fine bone powder, the demineralization solution was filtered (qualitative filter paper; Wet Strengthened Grades, Grade 91, 10 μm). While a magnetic bar was operated, 5M sodium hydroxide (NaOH) was slowly added while checking the pH level from time to time, and when the pH was 7.0 to 7.5, the neutralization process was stopped. The neutralized solution was centrifuged at 1,500 rpm for 5 minutes, a supernatant was removed, and then a pellet was washed with distilled water five times (1,500 rpm, centrifuged for 5 minutes each). The finally-obtained residue was lyophilized or dried at a high temperature (oven-dried).

A composite DBM composition was obtained by mixing the entire amounts of the processed DBM and the dried residue.

Experimental Example 1. Comparison of Yields and BMP-2 Contents of Composite DBM Compositions Using One-Step Process and a Two-Step Process Yields of the composite DBM composition prepared in the one-step process of Example 1 and the composite DBM composition prepared in the two-step process of Comparative Example 1 were compared.

FIG. 1A shows the result of comparing yields.

As shown in FIG. 1A, it can be confirmed that the composite DBM composition prepared by the unification process, that is, the one-step process, according to the present invention, compared to a two-step process for separately obtaining DBM and bone minerals, has a superior yield.

In addition, a BMP-2 content in the composite DBM composition prepared by the one-step process of Example 1 and a BMP-2 content in the composite DBM composition prepared by the two-step process of Comparative Example 1 was compared.

FIG. 1B shows the result of comparing BMP-2 contents.

As shown in FIG. 1B, it can be confirmed that the composite DBM composition prepared in the one-step process has an excellent BMP-2 content.

Experimental Example 2. Verification of Method of Obtaining Human-Derived Bone Mineral SEM Measurement of Bone Mineral A scanning electron microscopy (SEM) image of the bone mineral of the composite DBM composition obtained in Example 1 was obtained.

FIG. 2 shows the photographed image.

As shown in FIG. 2, it can be confirmed that the obtained bone mineral has a hexagonal pillar-shaped crystal structure that is generally possessed by natural bone minerals.

Experimental Example 4. Measurement of Calcium/Phosphorus (Ca/P) Content Ratio and the Mineral Content Ratio of Composite DBM Composition The composite DBM composition obtained in Example 1 consists of DBM, bone mineral and BMP-2. In this experimental example, the bone mineral was physically separated from the obtained composite DBM composition, and then the bone mineral content was analyzed.

Specifically, 10 to 50 ml of a 0.5 to 1.5N of hydrochloric acid solution per 1 g of the obtained material was used to lower the pH to 1 to 3, and then a supernatant was obtained, thereby obtaining a solution in which the bone mineral is dissolved. Afterward, a 0.5 to 4.0M sodium hydroxide (NaOH) solution was used such that the bone mineral was physically precipitated and separated. In addition, components of the bone mineral were analyzed from the resulting precipitate using an inductively coupled plasma spectrometer (ICP-OES. PerkinElmer, Optima 8300).

The analysis results are shown in Table 1 below.

TABLE 1

| *ICP-OES (PerkinElmer, Optima 8300) | | | | | | | | wt % |
|---|---|---|---|---|---|---|---|---|
| Element | Mg | | Ca | | P | | Fe | |
| Sample | Concentration | RSD % | Concentration | RSD % | Concentration | RSD % | Concentration | RSD % |
| HAP1 | 0.373 | 0.398 | 47.687 | 0.510 | 21.235 | 0.550 | <LOQ | |
| HAP2 | 0.369 | 0.303 | 42.158 | 0.920 | 18.520 | 1.360 | | |
| HAP3 | 0.364 | 0.849 | 34.698 | 0.150 | 15.514 | 0.230 | | |
| HAP4 | 0.358 | 0.641 | 34.736 | 0.850 | 15.199 | 1.030 | | |
| HAP5 | 0.366 | 1.754 | 34.369 | 2.350 | 15.394 | 1.780 | | |
| Element | Na | | K | | Zn | | | |
| Sample | Concentration | RSD % | Concentration | RSD % | Concentration | | RSD % | |
| HAP1 | 0.143 | 0.520 | <LOQ | | 0.015 | | 0.310 | |
| HAP2 | 0.079 | 0.780 | | | 0.014 | | 0.410 | |
| HAP3 | 0.082 | 0.660 | | | 0.015 | | 0.750 | |
| HAP4 | 0.079 | 0.500 | | | 0.015 | | 0.690 | |
| HAP5 | 0.101 | 0.560 | | | 0.015 | | 0.950 | |
| LOQ: Limit Of Quantitation, RSD %: Standar Deviation | | | | | | | | |
| LOQ (wt %) | | | | | | | | |
| | | Fe | | | | 0.00025 | | |
| | | k | | | | 0.01702 | | |

Experimental Example 3. X-Ray Diffraction (XRD) Pattern of Bone Mineral

An X-ray diffraction pattern of the bone mineral of the composite DBM composition obtained in Example 1 was measured to confirm the X-ray diffraction analysis result for the unique crystal structure of the bone mineral.

FIG. 3 shows the result of X-ray diffraction analysis for the unique crystal structure of the bone mineral.

As shown in FIG. 3, it can be confirmed that the peaks are shown at 2θ=25.9, 32.0 and 39.7, which are intrinsic characteristic peaks of the bone mineral.

The analysis results showed that the mineral content ratio of the composition is similar to that of bone minerals constituted in the human body in a natural state.

The calcium content percentage was 34.369 wt % to 47.687 wt %, the phosphorus content percentage was 15.199 wt % to 21.235 wt %, and based on these, the ratio of calcium and phosphorus, that is, a Ca/P value, was confirmed to be in a range of 2.245 to 2.265. In addition, as the minerals that can be present only in bio-derived bone minerals, a magnesium content percentage was 0.358 to 0.373 wt %, a sodium content percentage was 0.079 to 0.143 wt %, a zinc content percentage was 0.014 to 0.015 wt %, a potassium content percentage was 0.015 to 0.02 wt %, and an iron content percentage was 0.00015 to 0.0025 wt %.

Meanwhile, the composition obtained according to Example 1 was measured to be 0.45 g after a one-step process for obtaining bone minerals by demineralizing 1 g of bone powder as a raw material before demineralization. On the other hand, the composition obtained according to Example 1 was measured to be 0.21 g when a two-step process was performed (FIG. 1A). In addition, through a BMP-2 assay, the content of the extracted BMP-2 was measured to be 56 ng/g when the one-step process was performed, and measured to be 31 ng/g when the two-step process was performed (FIG. 1B).

Example 2. Preparation of Composition for Bone Grafting (Composite DBM Paste)

(1) Preparation of Hyaluronic Acid/Carboxymethylcellulose Excipient

A paste-type composition for bone grafting was prepared with the composite DBM composition obtained in Example 1. To this end, first, hyaluronic acid (sodium hyaluronate (HA) by Shiseido (CAS 9067-32-7), Japan) as a biopolymer consisting of N-acetylglucosamine and glucuronic acid and carboxymethylcellulose (sodium carboxymethyl cellulose (CMC), Sigma-Aldrich) was mixed with 1,4-butanediol diglycidyl ether (BDDE, Sigma-Aldrich) as a crosslinking agent, thereby preparing an HA-CMC excipient (carrier).

Specifically, 1 to 10 ml of BDDE was added to 100 ml of a 0.2N sodium hydroxide aqueous solution heated to 50° C., and a solution containing 1 to 10 g of CMC was mixed with a solution containing 1 to 10 g of HA. The mixed solution was heated at 50° C. for 3 hours and crosslinked. The crosslinked mixture was dialyzed using a dialysis tubing cellulose membrane (typical molecular weight cut-off=14,000. Sigma-Aldrich) at room temperature for 2 hours in a beaker filled with 5 L of phosphate-buffered saline (Lonza Walkersville, Inc.). Dialysis was performed at room temperature for 1 hour after the phosphate-buffered saline was replaced with 5 L of 50% EtOH, and then at room temperature for 72 hours using a dialysis tubing cellulose membrane after the beaker was filled with 5 L of sterile water. Afterward, the HA-CMC excipient was lyophilized and then ground (FIG. 4).

(2) Preparation of Composition for Bone Grafting (Composite DBM Paste)

A paste-type composite DBM composition was prepared to contain a powder-type composite DBM composition at 10 to 30 wt %.

First, an HA-CMC solution was prepared by mixing the dried HA-CMC excipient with sterilized physiological saline in a ratio of 1:9 to 9:1, and the powder-type composite DBM composition and the HA-CMC solution were finally mixed in a ratio of 1:9 to 9:1.

Subsequently, gamma-ray sterilization (25 kGy) was performed.

Through this, the composite DBM composition was prepared in the form of a paste.

Experimental Example 5. Confirmation of Complex Viscosity According to the Concentration of HA-CMC Excipient and Content of Powder-Type Composite DBM Composition The complex viscosity (shear rate mode Rheometer-AR) of the gamma-ray sterilized (25 kGy) composite DBM paste was measured. In addition, to find the optimum composition ratio that exhibits excellent moldability, the complex viscosity of the HA-CMC excipient alone, and the complex viscosity according to the content of the composite DBM composition mixed with the excipient were additionally measured.

The measurement results are shown in FIG. 5.

FIG. 5A shows the result of measuring the complex viscosities of HA-CMC solutions in which the HA-CMC excipient is adjusted to have three concentrations (5 wt %, 10 wt %, and 20 wt %).

As shown in FIG. 5A, it can be confirmed that when the content of the HA-CMC excipient is 20%, compared to other contents, a complex viscosity value is higher.

Therefore, a composite DBM paste was prepared by mixing the 20% HA-CMC excipient exhibiting a viscosity judged to be most suitable for moldability with a composite DBM composition powder. Here, the content of the powder-type composite DBM composition was adjusted to 10 to 30 wt %, and the complex viscosity of the paste was measured.

FIG. 5B shows the result of measuring complex viscosities when the composite DBM composition is adjusted to have three contents (10 wt %, 20 wt %, and 30 wt %).

As shown in FIG. 5B, when the composite DBM composition was contained at 30%, the complex viscosity was measured to be 65,000 Pa·s. This is a value that can have levels of moldability and cohesion judged to be appropriate as a bone graft material.

Experimental Example 6. Evaluation of In Vitro Osteoinductivity of Composite DBM Paste The osteoinductivity of the composite DBM paste prepared in Example 2 was evaluated.

Specifically, in vitro experiments were performed using MC3T3-E1 cells (cells isolated from calvaria preosteoblasts of C57BL/6 mouse embryo/fetus ATCC, CRL-2593, 2594, 2596, 2596) as preosteoblasts. An alkaline phosphatase activity assay (ALP-assay) was performed on the cell line using a composite DBM paste including the 30% composite DBM composition that is judged to have the most suitable moldability and maximum osteoinductivity (using HA-CMC solution containing 20% HA-CMC excipient). rhBMP-2 was used as a positive control, 10 mg of DBM was used as an active control, and an HA-CMC excipient was used as a negative control.

The evaluation result is shown in FIG. 6.

As shown in FIG. 6, when the composite DBM paste (composite DBM composition, 30%) according to the present invention was used, compared to the active control and the negative control, it was confirmed that the ALP activity is excellent.

Experimental Example 7. Evaluation of In Vivo Osteoinductivity of Composite DBM Paste Osteoinductivity was evaluated by implanting a composite DBM composition or a composite DBM paste into each of the left and right sides of the muscle pouches of the abdomen based on the midline of the spine of nude mice (BALB/c nude mice, male, weight of 22 g, 8 weeks old).

Here, as Experimental Group 1, a sample containing 30% of the composite DBM composition prepared in Example 1 (one-step DBM graft material), as Experimental Group 2, a sample containing 30% of the composite DBM composition prepared in Comparative Example 1 (two-step DBM graft material), as Experimental Group 3, a sample containing 25% of the composite DBM paste prepared in Example 2 (one-step composite DBM composition paste), and as Experimental Group 4, a commercial DBM medical device product containing DBM alone (commercial DBM graft material containing DBM alone) were used.

The degrees of bone regeneration was confirmed from images of tissue stained with hematoxylin and eosin, and quantitatively evaluated based on Table 2 by ASTM F 2529 13 "Standard guide for in vivo evaluation of the osteoinductive potential for materials containing demineralized bone (DBM)."

In the present invention, FIG. 7 shows the result of confirming the degrees of bone regeneration of the experimental groups from the histochemical images.

In addition, as a result of quantitative evaluation based on Table 2, as shown in FIG. 8, Experimental Group 3 containing bone mineral (one-step process composite DBM composition paste) showed 37% osteoinductivity, indicating level 4, Experimental Group 1 (one-step DBM graft material) showed 31% osteoinductivity, indicating level 4, Experimental Group 2 (Two-step DBM graft material) showed 20% osteoinductivity, indicating level 2. In addition, Experimental Group 4, the commercial DBM graft material, showed 30% osteoinductivity, indicating level 3. Therefore, it can be confirmed that Experimental Group 3, the one-step composite DBM composition paste, has relatively superior osteoinductivity compared to other Experimental Groups.

TABLE 2

| Level | Degree of Bone Regeneration |
|---|---|
| 0 | No bone formation |
| 1 | Less than 10% of new bone |
| 2 | 10% or more~less than 20% new bone |
| 3 | 20% or more~less than 30% new bone |
| 4 | 30% or more new bone |

ASTM F-2529-13 "Standard guide for in vivo evaluation of the osteoinductive potential for materials containing demineralized bone (DBM)"

Test specification

Evaluate the H&E image of the DBM graft by dividing it into 5 × 5 grids
★ = Square not calculated
(square not including implant bone and new bone-forming elements)
★ & ☆ = square included in calculation
(square including implant bone and new bone-formingg elements)
★ = Square including implant bone
☆ = Square including new bone-forming elements
(Total Number of Squares with New Bone Forming Elements)/(Total Number of Squares with Implant Bone/New Bone Forming Elements) × 100
Level 0 = no implant detected
1 = <10% new bone forming elements
2 = 10-20% new bone forming elements
3 = 21-30% new bone forming elements
4 = >30% new bone forming elements

INDUSTRIAL AVAILABILITY

Since a composite demineralized bone matrix (DBM) composition prepared by a one-step process according to the present invention contains bone minerals obtained from the bio-derived bone in the composition ratio of the original bone, it can provide a mineral content condition closest to the bone-forming environment in the body and thus is more stable. In addition, the composition contains sufficient amounts of proteins effective in bone growth and bone formation and thus has excellent osteoconductivity and osteoinductivity. Accordingly, the composition can impart an excellent bone formation effect.

Moreover, in the present invention, since the composite DBM composition is mixed with a hydrogel-type excipient, when being implanted in the body, it can maximize bone formation when the composition of the present invention is implanted into the body while being well agglomerated based on an affected area without being scattered in a powder state, and impart biocompatibility.

The invention claimed is:

1. A method of preparing a composite demineralized bone matrix (DBM) composition using a one-step process, comprising:
    a demineralization step of demineralizing bone tissue with an acidic solution;
    a bone mineral precipitation step of precipitating bone mineral by neutralizing the demineralized solution with an alkaline solution;
    a bone morphogenetic protein-2 (BMP-2) extraction step of extracting BMP-2 by centrifuging the solution in which the precipitation is completed and adding an acidic solution to a pellet; and
    a composite DBM composition preparation step of precipitating the DBM, the bone mineral, and the BMP-2 by neutralizing the BMP-2-extracted solution with an alkaline solution.

2. The method of claim 1, wherein the bone tissue is cortical bone, and has an average particle diameter of 20 to 800 μm.

3. The method of claim 1, wherein the demineralization step is performed by demineralization with 10 to 50 ml of a 0.5 to 1.5N hydrochloric solution per 1 g of the bone tissue.

4. The method of claim 1, wherein the bone mineral precipitation step is performed by neutralization with a 0.5 to 4.0M sodium hydroxide (NaOH) solution.

5. The method of claim 1, wherein the BMP-2 extraction step is performed by adding acetic acid to the pellet.

6. The method of claim 1, wherein the composite DBM composition preparation step is to precipitate DBM, the bone mineral and BMP-2 by neutralization with a 0.5 to 4.0M sodium hydroxide (NaOH) solution.

7. The method of claim 1, further comprises:
    drying the resulting precipitate, after the composite DBM composition preparation step.

* * * * *